United States Patent [19]
Collas et al.

[11] Patent Number: 4,918,220

[45] Date of Patent: Apr. 17, 1990

[54] SEPARATION OF TOLUENE DIISOCYANATE FROM THE RESIDUES OF THE PRODUCTION THEREOF

[75] Inventors: Gerard Collas, Caluire; Georges Gros, Bourg La Reine; Ferenc Sagi, Lyons, all of France

[73] Assignee: Rhone-Poulenc Chimie, Courbevoie, France

[21] Appl. No.: 296,810

[22] Filed: Jan. 13, 1989

[30] Foreign Application Priority Data

Jan. 13, 1988 [FR] France .................................. 88 00466

[51] Int. Cl.$^4$ ........................................... C07C 137/00
[52] U.S. Cl. ...................... 560/352; 560/347
[58] Field of Search .................... 560/352, 347

[56] References Cited

U.S. PATENT DOCUMENTS

4,372,891  2/1983  Hilbert et al. ................... 560/352

OTHER PUBLICATIONS

Chem. Abst. Hyatt, vol. 102 (1985), p. 102:24047h.
Chem. Abst. Winter, vol. 93 (1980), p. 93:152230h.
Journal of Organic Chemistry 1984, 49, 5097–5101, "Liquid and Supercritical Carbon Dioxide as Organic Solvents".

*Primary Examiner*—Alan Siegel
*Attorney, Agent, or Firm*—Burns, Doane, Swecker & Mathis

[57] ABSTRACT

Toluene diisocyanate (TDI) is separated and recovered from the residues of the production thereof, e.g., from the tars of phosgenation of an aromatic diamine, by extracting such residues with an extractant which comprises an inert gas, e.g., $CO_2$, in either the liquid or supercritical state, optionally in the presence of a coextractant diluent, for example an ester, aromatic hydrocarbon or chlorinated aromatic hydrocarbon, or chlorinated aliphatic hydrocarbon.

20 Claims, No Drawings

SEPARATION OF TOLUENE DIISOCYANATE FROM THE RESIDUES OF THE PRODUCTION THEREOF

BACKGROUND OF THE INVENTION

1. Field of the Invention

The present invention relates to the separation and recovery of toluene diisocyanate (TDI) from the residues from its manufacture.

2. Description of the Prior Art

It is well known to this art that appreciable amounts of heavy compounds are formed during the manufacture of TDI. These amounts, which can vary depending on the precise nature of the manufacturing process employed, generally represent from 10 to 15% by weight, or even more. These heavy compounds are usually concentrated by distillation of TDI, typically to a concentration of 30 to 40% of TDI and from 60 to 70% of heavy compounds.

It is difficult to continue the distillation in order to obtain mixtures with higher concentrations of heavy compounds, because of the increase in the viscosity of the mixture. Other techniques must therefore be employed to recover the TDI present in a mixture of this type, to dispose of a combustible residue containing the heavy compounds in question and no longer containing any TDI, and to avoid both contamination with toxic vapors and costly losses of final product.

Various such techniques have already been proposed to this art, but each has at least one of the following disadvantages:

(a) it is noncontinuous;

(b) it is costly in raw material and/or in energy requirements;

(c) it is very difficult to implement on an industrial scale.

An analysis of these various proposed techniques of the specific disadvantages which they exhibit is set forth in the preamble of European Patent No. 0,000,463, which also proposes a specific solution to this problem, namely:

continuous treatment of residues from this manufacture in a stirred and scraped evaporator, at a temperature commencing at 100°–130° C., at a pressure of 666.5 to 2,666 Pa, a temperature which is then progressively raised to a temperature of 220° to 260° C. with a minimum residence time of 15 min in the evaporator, in order to evaporate the TDI while continuously removing the residues, especially by utilizing an extrusion system.

According to said '463 European patent, the process described, which enables good results to be achieved on an industrial scale, nevertheless exhibits the following disadvantages: satisfactory operation thereof demands strict controls both of the physicochemical conditions (pressure, temperature, residence time) and of the mechanical conditions (stirring, transport of the products of increasing viscosity in the evaporator, scraping).

In fact, the smallest deviation from these conditions is liable to cause either a polymerization which can progress until the residue sets solid in the apparatus, or a decomposition of TDI into gases which generate foam in the viscous residual mixture.

Also, the movement of the viscous residue along the wall of the evaporator must be controlled such that the temperature can be increased in step with the evaporation of the TDI, in order to complete said evaporation without running the risk of decomposition.

Furthermore, in use, this particular process is found to exhibit the following additional disadvantage. Its operation is feasible only in the case of certain categories of residues, namely, those which present an increasing viscosity profile in step with the progress of the evaporation of TDI. In the case of residues from industrial manufacture which do not exhibit a profile of this kind, the process in question cannot be applied.

Thus, need continues to exist for a process for the separation of the TDI present in the residues from its manufacture and which is capable of being carried out continuously, independently of the nature or of the precise origin of the residues to be treated, which is both efficient, simple to implement on an industrial scale and low in cost and which, where appropriate, gives rise to a final waste in a form which can be easily handled.

SUMMARY OF THE INVENTION

Accordingly, a major object of the present invention is the provision of an improved process for the separation of toluene diisocyanate present in the residues from the production thereof, which improved process features extracting such residues with an inert gas in either the liquid or supercritical state.

DETAILED DESCRIPTION OF THE PREFERRED EMBODIMENTS OF THE INVENTION

More particularly according to the present invention, residues from the manufacture of TDI can vary in appearance or composition, in practice. In fact, when TDI (a mixture of the 2,4- and 2,6-isomers of diisocyanatotoluene) is produced by phosgenation of toluenediamine (mixture of the 2,4- and 2,6-isomers in a proportion of 80 parts of the former to 20 parts of the latter, approximately), for example in ortho-dichlorobenzene as reaction diluent, the reaction mixture is subjected to at least one distillation in order to remove hydrochloric acid, residual phosgene and at least part of the reaction diluent therefrom. There remains, therefore, a mixture consisting of 8 to 20% (wt) of TDI and of 0.5 to 3% of heavy products, the balance to 100% being ortho-dichlorobenzene.

This mixture may be concentrated by removing the ortho-dichlorobenzene contained therein. It then contains only heavy products and TDI. The residue freed from orthodichlorobenzene can, in turn, be concentrated as indicated hereinbefore, by distillation of TDI, it being possible for a typical concentration to reach from 50 to 70% of heavy compounds in the case of 30 to 50% of TDI. This residue, which is both concentrated and freed from ortho-dichlorobenzene, is in the form of tars whose softening point ranges from approximately 200° to 250° C.

Although these various types of residues may be treated according to the process of the present invention, said process is particularly advantageous for treating residual mixtures whose composition is as follows:

(a) from 5 to 100% by weight of a mixture of:
(i) from 95 to 50% by weight of TDI, and
(ii) from 5 to 50% by weight of heavy products; and
(b) from 0 to 95% by weight of a diluent.

Naturally, when a diluent is present in the residual mixture to be treated, it is advantageously the diluent from the phosgenation reaction. The diluent employed is typically an aromatic or chlorinated aromatic hydrocarbon compound such as toluene, monochlorobenzene and orthodichlorobenzene. Nevertheless, other diluents may be used, especially esters such as ethyl, isopropyl, butyl or isobutyl phthalate, or the corresponding isophthalate, butyl or isobutyl adipate, methyl, ethyl, butyl or isobutyl butyrate or isobutyrate, 2-ethylhexyl 2-ethylhexanoate, or other chlorinated hydrocarbons such as methylene chloride and, in particular, 1,2,4-trichlorobenzene.

When a diluent is present in the residual mixture to be treated, which constitutes a particularly advantageous embodiment of the subject process, it preferably represents from 5 to 30% (by weight) of the composition.

It has, therefore, now unexpectedly been found that the separation of the TDI present in the residues from the manufacture thereof is easy to carry out, by treating such residue with an inert gas in the liquid or supercritical state. Exemplary of such inert gases, representative are carbon dioxide, butane, ethane, propane, ethylene, nitrous oxide, $SF_6$ and the Freons. Carbon dioxide, which is cheap, nontoxic and nonflammable, is the compound of choice. It has also been found that supercritical $CO_2$ dissolves and suitable extracts the TDI present in the "condensate".

It too has been found that the separation operation in question and, in particular, extraction with carbon dioxide in the liquid or supercritical state, is advantageously carried out in the presence of a coextractant selected from among the diluents for the phosgenation reaction, it being possible for the coextractant to be different in kind from the diluent employed for carrying out said reaction.

The coextractant generally constitutes from 5 to 70% (wt) of the carbon dioxide in the liquid or supercritical state, and preferably at least 10% (wt) of said gas. No particular advantage is noted when this content exceeds 30% (wt) of the carbon dioxide in the liquid or supercritical state.

The coextractant is advantageously selected from among toluene, ortho-dichlorobenzene, 1,2,4-trichlorobenzene and monochlorobenzene.

The coextractant is advantageously of the same kind as the diluent employed during the manufacture of TDI by phosgenation of the corresponding diamine, as above indicated. In practice, to satisfactorily carry out the process according to the invention, the amount of coextractant will be proportionally higher, the smaller the proportion of diluent in the residue to be treated.

Indeed, it has now been determined that in the presence of a coextractant of this kind the final waste contains TDI in amounts which are markedly lower than those contained in the waste produced in the absence of a coextractant of such type.

Moreover, in the presence of a coextractant of this kind, the risk of gelling of the mixture in the extraction column is considerably reduced.

The process according to the present invention comprises, therefore, a treatment of residues as defined above with an inert gas in the liquid or supercritical state, which is advantageously carbon dioxide. Where appropriate, this extraction is carried out in the presence of a coextractant, as described above; the conditions applicable in the case of $CO_2$ alone are also applicable in this particular embodiment.

The extraction may be carried out continuously or noncontinuously.

In the liquid state, $CO_2$ is used at a temperature of from 0° to 31° C., and a pressure of from 30 to 500 bars. It is often preferable to conduct the operation at a temperature of from 20° to 31° C. when the viscosity of the residue is high. The pressure may range from 60 to 300 bars.

This extraction may be carried out in the supercritical state at a temperature above 31.4° C. (critical temperature of $CO_2$) and at a pressure of from 73 to 500 bars. The temperature preferably ranges from 31.4° C. to 100° C. and the pressure from 73 to 350 bars.

The residue containing TDI is treated with $CO_2$ which is liquid or in the supercritical state; the operation may be carried out noncontinuously, that is to say, by mixing the residue in a reactor with $CO_2$ in the liquid or supercritical state.

In general, it is preferred to use the extraction gas in the supercritical state in the process according to the invention.

The extraction may be carried out continuously in a conventional manner, in an apparatus known per se.

The extraction gas in the liquid or supercritical state is injected into the extraction apparatus, which may be, for example, a column filled with a packing permitting better contact between the residue and the extraction gas. The residue may be introduced at the other end of the column; a countercurrentwise extraction is then carried out. Less frequently, it may be introduced at the same end as the extraction gas; a cocurrent extraction is then carried out. The waste is recovered at one end of the extraction column, while the extraction gas containing TDI and, if appropriate, coextractant is treated in order to separate it from the extracted products.

This may be accomplished either by decreasing its pressure or by increasing its temperature, or by both decreasing its pressure and increasing its temperature. The purpose of these conditions is to modify the solvent capacity of the extraction gas.

The pressure decrease or expansion may be carried out in one or more steps and the extraction gas may be expanded down to a pressure equal to atmospheric pressure, or down to a higher pressure, at which it will be recycled in the case of a continuous process.

In fact, if the extraction gas is recycled, it is economically preferable not to expand it down to atmospheric pressure, since this would require a greater expenditure of energy to recompress it in the cycle following the process. It is preferable to expand it down to a pressure at which the extracted compounds are insoluble, or very poorly soluble.

The waste liquefied by the extraction gas and the coextractant in the column is liable to gel or to solidify when the expansion is carried out without special precautions. However, the expansion may be carried out in a controlled manner, or even in a carrier liquid, and the waste in question may be obtained in the form of a solution or a dispersion which is easily handled.

Various embodiments of the invention will become apparent to those skilled in this art, among which there will be mentioned, as an alternative form of the present process, the embodiment according to which the column is initially at least partially filled with the residue to be treated, through which the $CO_2$ will be bubbled, if appropriate, with the coextractant countercurrentwise to the residue feed and, as a preferred alternative form of the present process, the embodiment according to which the column is initially at least partly filled with $CO_2$, if appropriate, mixed with a coextractant, the residue feed, if appropriate diluted in the coextractant, being introduced at the head of the column.

The process above described permits the treatment, in particular, of residues obtained before the distillation of TDI in order to concentrate them; with an appropriate choice of a coextractant such as ortho-dichlorobenzene, it also makes it possible to carry out the treatment and to recycle the coextractant to the manufacture of TDI, which represents a marked advantage vis-a-vis the prior art.

In order to further illustrate the present invention and the advantages thereof, the following specific examples are given, it being understood that same are intended only as illustrative and in nowise limitative.

EXAMPLE 1:

250 g of tars having the following composition were introduced into a stainless steel column 16 mm in diameter and 70 mm in height, filled with a packing of glass Raschig rings (6 mm × 6 mm):
(i) ortho-dichlorobenzene 9% (wt)
(ii) TDI 55% (wt)
(iii) heavy compounds 36% (wt).

The column was thermostated at a temperature of 50° C., and $CO_2$ in the supercritical state was then admitted up to a pressure of 190 bars. This pressure was controlled by a pressure relief valve at a pressure of 190 bars throughout the test.

When the total system was at equilibrium, carbon dioxide in the supercritical state, at a rate of approximately 1100 g/h, and ortho-dichlorobenzene (ODCB), at a rate of 350 g/h, were introduced simultaneously at the base of the column.

The extracts were recovered, beyond the pressure relief valve, in successive powder flasks at atmospheric pressure.

When the ratio (weight of $CO_2$ introduced/charge) was equal to 50, the composition of the residue in the column was as follows:
(i) ortho-dichlorobenzene = 33% (wt)
(ii) TDI = 0.8% (wt)
(iii) heavy ends = 66.2% (wt).

At this stage, the test was continued by introducing the tars continuously at the head of the column, at a flow rate of 23 g/h.

At the base of the column, $CO_2$ and ODCB were fed together, at flow rates of 1100 g/h and 330 g/h respectively, namely, in an ODCB/$CO_2$ ratio of 30/100, and the product to be treated was introduced. Beyond the pressure control weir, the extract recovered at atmospheric pressure, at a rate of approximately 320 g/h, contained approximately 4% of TDI and 96% of ODCB.

The extraction residue recovered at the base of the column had a TDI content of 1.2% (wt), the remainder being ODCB (33% wt) and heavy ends (65.8% wt).

EXAMPLE 2:

Using the extraction column described in Example 1 and the same conditions of pressure and temperature, a mixture of $CO_2$ and of ODCB was introduced continuously at the base of the column, at flow rates of 1250 g/h and 350 g/h respectively, namely, in an ODCB/$CO_2$ ratio of 28/100.

Tars which were identical in composition with those of Example 1 were fed continuously and countercurrently at the head of the column; flow rate = 100 g/h; the $CO_2$ flow rate/feed flow rate ratio was therefore 12.5.

Under these conditions, an extraction residue whose composition by weight was as follows was recovered continuously at the base of the column:
(i) ODCB = 48%
(ii) TDI = 2.3%
(iii) heavy ends = 50.2%.

EXAMPLE 3:

Using the extraction column described in Example 1 and similar pressure and temperature conditions (200 bars; 50° C.), a mixture of $CO_2$ and of ODCB was introduced simultaneously at the base of the column, at flow rates of 1125 g/h and 180 g/h respectively, namely, in an ODCB/$CO_2$ ratio of 16/100.

TDI tars whose composition was as follows:
(a) 50% (wt) of TDI
(b) 50% of tars
were fed continuously and countercurrently into the head of the column.

The flow rate was set at 21.5 g/h. After the operation of the column had reached equilibrium, a sample of the residue contained 1.7% of residual TDI.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the separation of toluene diisocyanate from the residues of the production thereof, comprising extracting such residues with an extractant which comprises an inert gas in either the liquid or supercritical state wherein the inert gas comprises carbon dioxide, butane, ethane, propane, ethylene, nitrous oxide, $SF_6$, or a Freon.

2. The process as defined by claim 1, said extractant further comprising a diluent.

3. The process as defined by claim 1, said residues comprising from 5% to 100% by weight of a mixture of 95% to 50% by weight of toluene diisocyanate and 5% to 50% by weight of heavy products, and from 0% to 95% by weight of a diluent.

4. The process as defined by claim 3, said residues comprising a diluent.

5. The process as defined by claim 4, said diluent comprising toluene, ortho-dichlorobenzene, 1,2,4-trichlorobenzene or monochlorobenzene.

6. The process as defined by claim 5, said diluent comprising ortho-dichlorobenzene.

7. The process as defined by claim 4, said diluent comprising from 5% to 30% by weight of the extractant.

8. The process as defined by claim 1, said extractant comprising carbon dioxide in either the liquid or supercritical state.

9. The process as defined by claim 8, said extractant comprising carbon dioxide in the supercritical state.

10. The process as defined by claim 8, said toluene diisocyanate having been produced by phosgenation of an aromatic diamine in the presence of a diluent, and said extractant also comprising a phosgenation diluent coextractant.

11. The process as defined by claim 10, wherein the diluent of phosgenation differs from the coextractant diluent.

12. The process as defined by claim 10, said coextractant diluent comprising toluene, ortho-dichlorobenzene, 1,2,4-trichlorobenzene, or monochlorobenzene.

13. The process as defined by claim 10, said coextractant diluent comprising from 5% to 70% by weight of the carbon dioxide in either the liquid or supercritical state.

14. The process as defined by claim 13, said coextractant diluent comprising at least 10% by weight of the carbon dioxide in either the liquid or supercritical state.

15. The process as defined by claim 12, said coextractant diluent comprising ortho-dichlorobenzene.

16. The process as defined by claim 10, wherein the diluent of phosgenation is the same as the coextractant diluent.

17. The process as defined by claim 8, carried out at a temperature of from 0° to 31° C. and at a pressure of from 30 to 500 bars.

18. The process as defined by claim 17, carried out at a temperature of from 20° to 31° C. and at a pressure of from 60 to 300 bars.

19. The process as defined by claim 8, carried out at a temperature above the critical temperature of carbon dioxide and at a pressure of from 73 to 500 bars.

20. The process as defined by claim 19, carried out at a temperature of less than 100° C. and at a pressure of from 73 to 350 bars.

* * * * *